United States Patent [19]

Hines et al.

[11] Patent Number: 5,349,190
[45] Date of Patent: Sep. 20, 1994

[54] ADJUSTABLE TRIPLE-DETECTOR IMAGE DATA ACQUISITION SYSTEM

[75] Inventors: Horace Hines, San Jose; Paul Hug, Saratoga; Mark L. Lamp, San Jose, all of Calif.

[73] Assignee: ADAC Laboratories, Milpitas, Calif.

[21] Appl. No.: 801,551

[22] Filed: Dec. 2, 1991

[51] Int. Cl.$^5$ .............................................. G01T 1/166
[52] U.S. Cl. .......................... 250/363.05; 250/363.08
[58] Field of Search ..................... 250/363.05, 363.08, 250/363.10, 363.04, 363.05, 363.02

[56] References Cited

U.S. PATENT DOCUMENTS

| 4,943,726 | 7/1990 | Plummer | 250/363.05 |
| 5,206,512 | 4/1993 | Iwao | 250/363.05 |

FOREIGN PATENT DOCUMENTS 1278587 6/1972 United Kingdom ........... 250/363.08

OTHER PUBLICATIONS

Lim et al. "Triangular SPECT System for 3-D Total Organ Volume Imaging: Design Concept and Preliminary Imaging Results", IEEE Trans. Nucl. Sci., NS-32 (1), Feb. 1985, pp. 741–747.

*Primary Examiner*—Carolyn E. Fields
*Attorney, Agent, or Firm*—Townsend and Townsend Khourie and Crew

[57] ABSTRACT

An image data acquisition system for performing SPECT imaging and other types of imaging used in nuclear medicine includes an assembly of three detectors and a mechanical system for adjusting the relative angles of the detector image direction arrows, displacing the individual detectors along the image direction arrows, and rotating and displacing the detector assembly.

11 Claims, 9 Drawing Sheets

A.
FOCAL POINT

B.

C.

A.

B.

C.

A.

B.

C.

ADJUSTABLE TRIPLE-DETECTOR IMAGE DATA ACQUISITION SYSTEM

BACKGROUND OF THE INVENTION

1. Field of the Invention

The present invention relates generally to imaging systems and more particularly to imaging systems for use in nuclear medicine.

2. Description of the Relevant Art

Gamma ray cameras are used in nuclear medicine to generate high quality images for brain, SPECT (Single Photon Emission Computer Tomograph), and total body bone studies. These cameras are most frequently used for cardiac and total body bone studies.

It is very important that the gamma ray camera be designed for high patient throughput for both economic and therapeutic reasons. The cost for diagnosing each patient is reduced if more patients can be diagnosed per unit time. For very sick patients or patients in intensive care it is important to minimize the time required to acquire image data. Patient throughput is increased if imaging time is reduced. Other factors, such a patient set-up time also affect patient throughput.

Modern gamma ray cameras utilize detectors, such as Anger cameras, having a wide field of view so that it is possible to image the full width of the body of a patient at each angular stop without the requirement of rectilinear scanning. These detectors use thick lead collimators to focus images and are thus very heavy. The collimators must be positioned as close to the patient as possible to acquire image data required to generate high resolution images. The image data acquired by the detectors is processed by a computer to generate an image. Techniques for processing image data are well-know in the art and described in "Principles of Instrumentation in SPECT" by Robert Eisner. *Journal of Nuclear Medicine*, Vol. 13, #1, March 1985, pp. 23–31; "Computed Tomography in Nuclear Medicine" by John Keyes, (chapter in) *Computer Methods*, C. V. Mosley, St. Louis, 1977, pp. 130–138; and "Single Photon Emission Computed Tomography," by Bernard Oppenheim and Robert Appledown, (chapter in) *Effective Use of Computers in Nuclear Medicine*, Michael Gelfand and Stephen Thomas, McGraw-Hill Book Co., New York 1988, pp. 31–74.

Recent technological innovations have produced dual-head systems, with two detectors having their detector image direction arrows oriented at a fixed angle of 180°, and triple-head systems, with three detectors having their image direction arrows oriented at fixed angles of 120°, SPECT gamma ray cameras capable of rapid, high quality SPECT imaging. FIGS. 1A and 1B are schematic diagrams depicting the fixed orientation of the detector image direction arrows 2 of the detectors 4 in a dual-head and triple-head system.

When the detectors rotate about the patient, a lateral axis is defined as the mechanical axis of rotation aligned with the computer matrix for reconstructing the SPECT images.

The existing, fixed-angle single, dual, and triple head cameras each have certain features which are advantageous for a particular type of application. To determine which system is best for a particular application factors such as 1) the ability of the camera to perform required imaging tasks; 2) the quality of the images generated; and 3) patient throughput are evaluated.

The acquisition of data for a total body scan requires movement of the detector along the length of the patient's body. The dual-head system is very efficient because image data for anterior/posterior images can be acquired simultaneously. The time required to complete a scan can be reduced from 45 to 60 minutes, for a single-head camera, to 30 minutes. The triple-head system is no more efficient than the single-head system because the detectors cannot be aligned to acquire simultaneous anterior/posterior or left/right lateral data.

To generate high-quality SPECT for brain, bone, or liver studies views taken along a complete 360° circle (360° scan) around the body of the patient are required. Typically, about 64 to 128 angular stops are required to acquire the image data. The above-described dual-head camera reduces the imaging time to ½ the imaging time of a single-head system because data is acquired from two stops simultaneously. The triple-head camera reduces the imaging time to about ⅓ the imaging time of a single-head system because data is acquired from three stops simultaneously.

For cardiac SPECT studies, the analysis of complex imaging considerations has led to the use of at least 32 stops over a 180° arc about the patient's body (180° scan). For a 180° scan the imaging time of a single-head and dual-head system are the same because only one detector of the dual-head system is within the 180° arc at any given time. A triple-head system reduces the image time so that it is about ⅔ the time of a single-head system for a 180° scan because two detectors are within the 180° arc about ⅓ of the time.

In view of the above it is apparent that the mechanical system for orienting the detectors must be designed to provide a mechanism for accurately orienting the detectors at various angular stops relative to the patient and to position the collimator as close to the patient as possible. Additionally, the system must be stable so that the heavy detectors are held still at each stop to facilitate the acquisition of accurate imaging data. Other attributes that are required of the mechanical system are ease of patient positioning, size of footprint, and overall size of the system.

Further, as described above, the existing systems each have advantages for particular applications but generally lack the flexibility for optimal performance over a range of applications. Additionally, although cardiac SPECT imaging accounts for about 33% of the use of gamma ray cameras, none of the systems significantly reduce the imaging time for the 180° scan used in forming cardiac SPECT images.

SUMMARY OF THE INVENTION

The present invention is a triple-detector image data acquisition system designed to efficiently perform 180° cardiac and other SPECT data acquisition to generate high-resolution images while reducing the time required to acquire image data. The system can also be utilized to simultaneously acquire data for three static images, e.g., anterior, left anterior oblique, and right anterior oblique.

According to one aspect of the invention, the three detectors are mounted on a support structure so that their image direction arrows are oriented along a first plane perpendicular to the lateral axis and so that the angular displacement between the image direction arrows can be adjusted. This allows smaller organs, such as the brain, to be imaged by keeping the collimators as close as possible to the body of the patient.

According to another aspect of the invention, the detectors can be displaced along the direction of their image direction arrows.

According to a further aspect of the invention, the support structure can be angularly displaced about the lateral axis.

According to a still further aspect of the invention, the support structure can be displaced toward or away from the lateral axis.

According to a further aspect of the invention, a detector is provided with a slanted collimator to facilitate placing the detector closer to an object-to-be-imaged to improve image resolution.

Other features and advantages of the invention will become apparent in view of the attached drawing and following detailed description.

DETAILED DESCRIPTION OF THE PREFERRED EMBODIMENTS

Figure 1A:
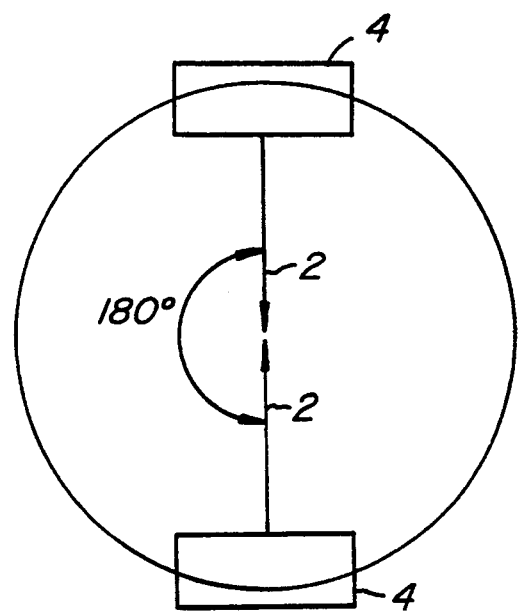
FIGS. 1A and 1B are schematic views depicting the fixed orientation of the detectors for existing dual-head and triple-head detectors.
Figure 1B:
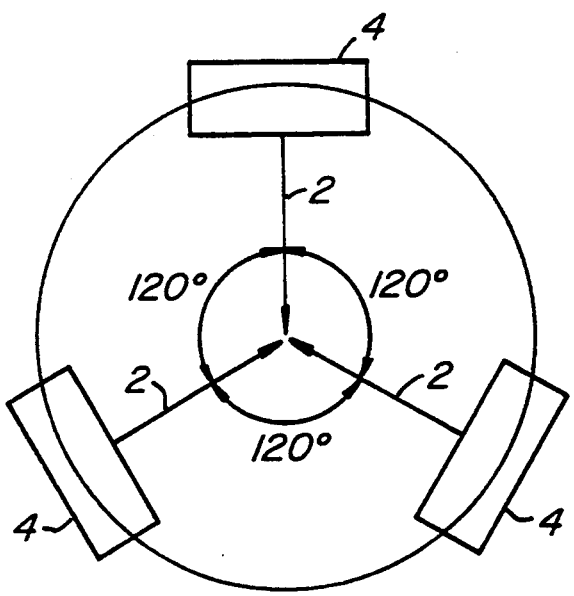
Figure 2A:
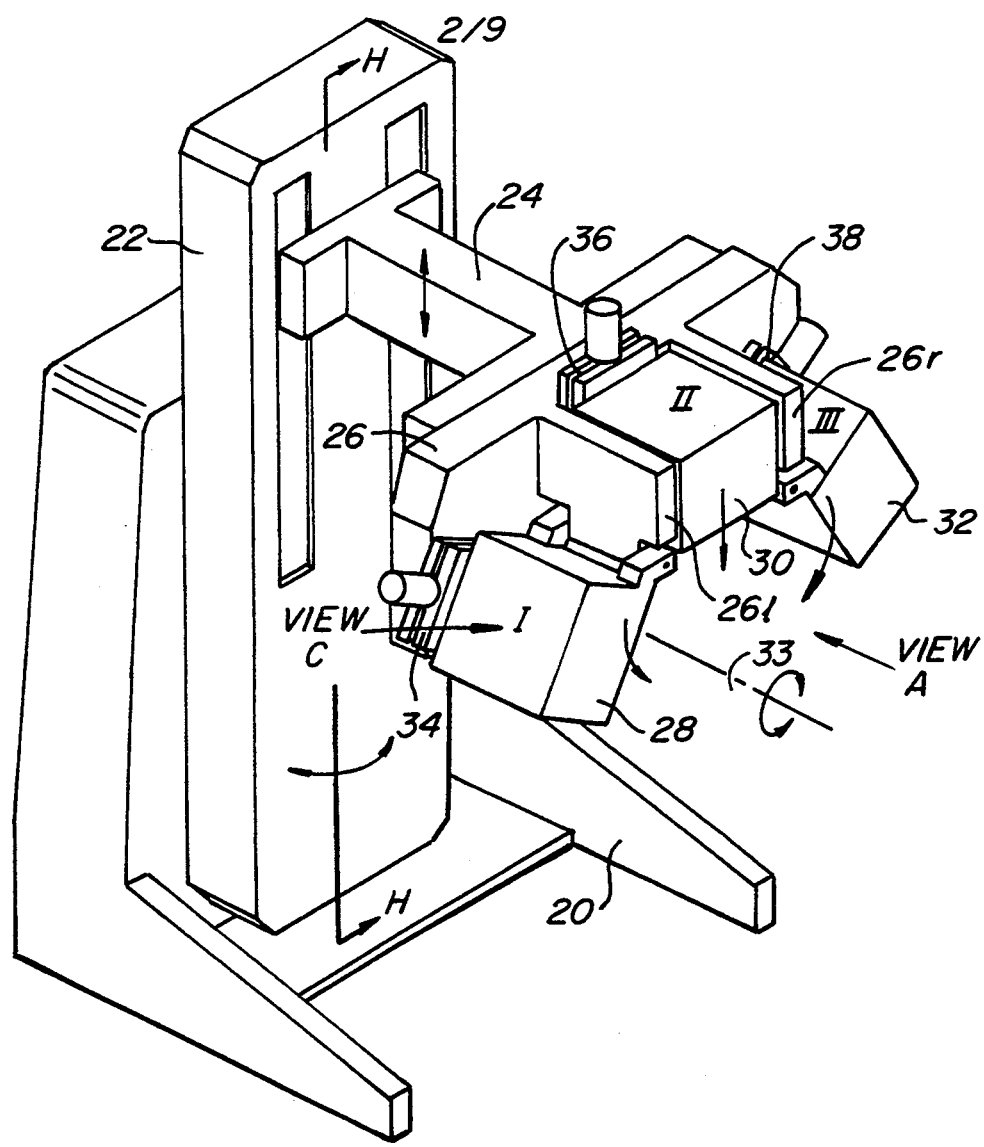
FIG. 2A is a perspective view of a preferred embodiment of the invention.

FIG. 2A is a perspective view of a preferred embodiment of the invention. The embodiment depicted in FIG. 2A is a triple-head SPECT data acquisition system that permits both angular and radial motion of the detector assembly as well as independent adjustment of the relative angles of the detector image arrows and the distance of the detectors from an object-to-be-imaged. Detailed descriptions of the mechanisms for providing the various types of motion will be described below with reference to FIGS. 2-10.

In FIG. 2A, a base 20 supports a rotatable arm 22 having a support beam 24 movably coupled thereto. A detector support structure 26, having left and right gussets 26*l* and 26*r*, is connected to the support beam 24. A first detector support frame 28 is pivotally mounted to the left gusset 26*l*, a second detector support frame 30 is mounted between the left and right gussets 26*l* and 26*r*, and a third detector support frame 32 is pivotally mounted to the right gusset 26*r*.

First, second, and third detector radial motion mechanisms 34, 36, and 38 are coupled to the first, second, and third detector support frames 28, 30, and 32, respectively.

In operation, the angular orientation relative to the lateral axis 33 of the entire detector assembly is adjusted by rotating the arm 22 and the distance of the detector assembly from the lateral axis is adjusted by moving the support beam 24 along the arm 22. The relative angular positions of the detectors is adjusted by pivoting the first and third detector support frames 28 and 32 and the distance of each detector from an object to be imaged is independently adjusted by the radial motion mechanisms 34, 36, and 38.

Figure 2B:
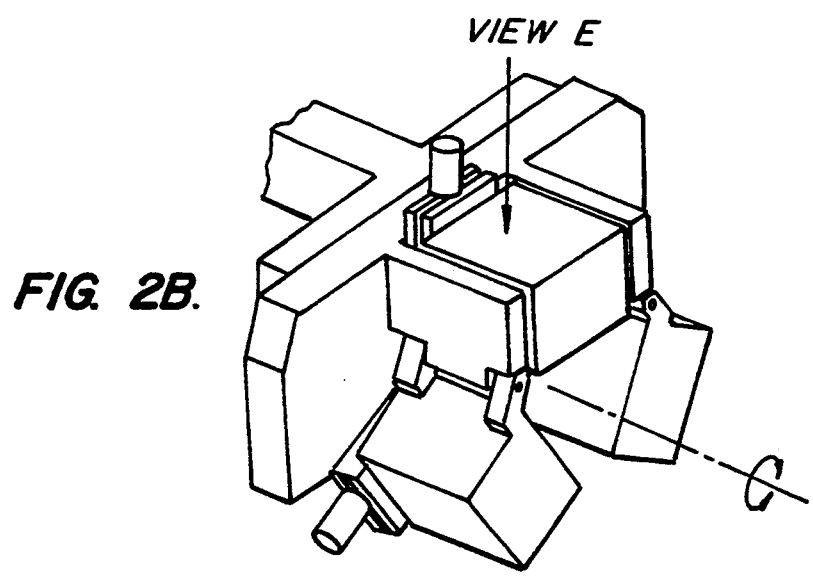
FIG. 2B depicts the detectors oriented at 60°.

In FIG. 2A the detectors are shown oriented with their image direction arrows having a relative angular displacement of 60°. In FIG. 2B the detectors are oriented with their image direction arrows having a relative angular displacement of 120°.

The mechanism for pivoting the first and third detector support frames 28 and 32 to change the angular displacement between the detector image direction arrows will now be described with reference to FIGS. 3, 4, and 5.

Figure 3:
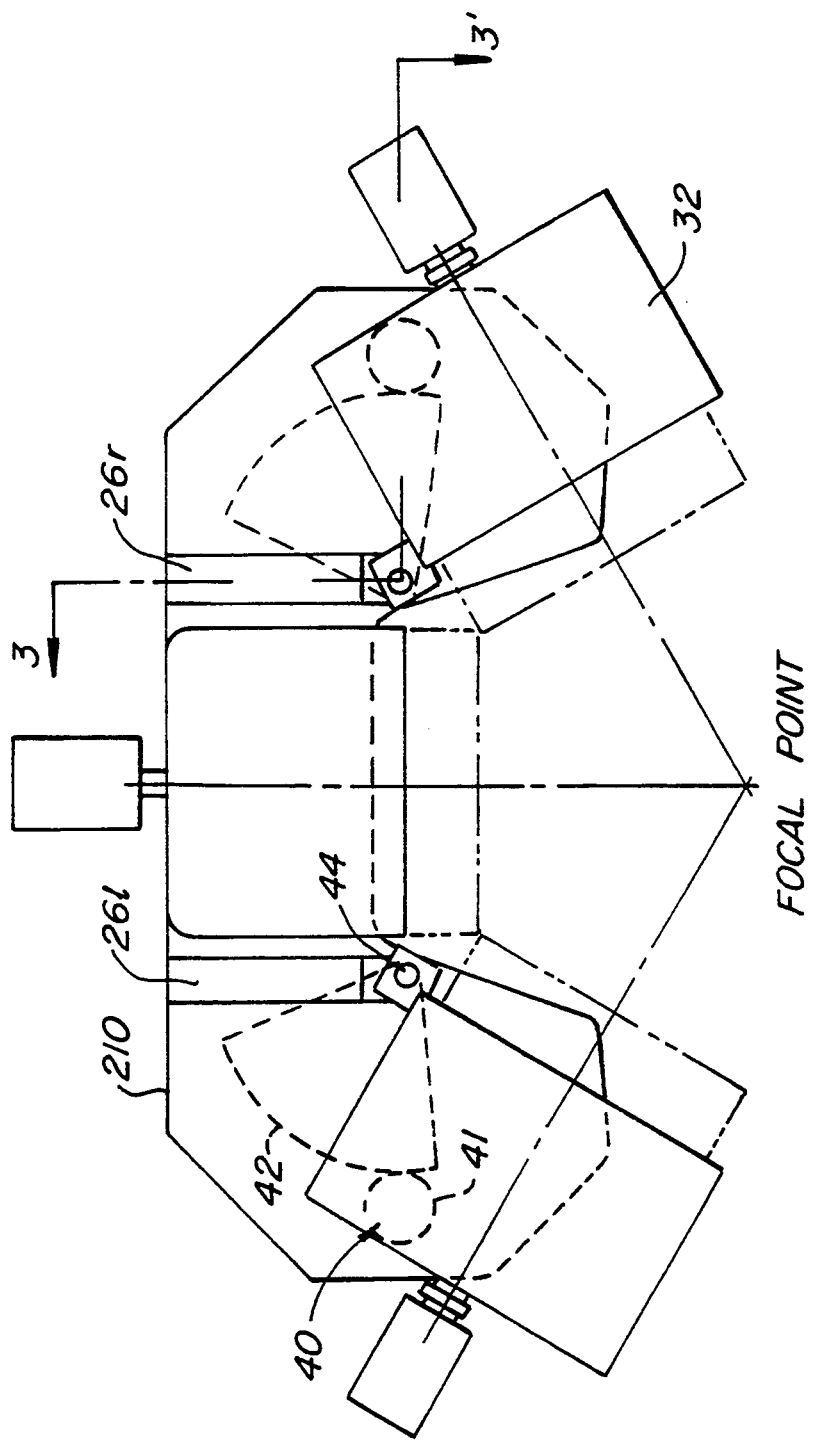
FIG. 3 is a schematic diagram taken along view A of FIG. 2A.
Figure 4:
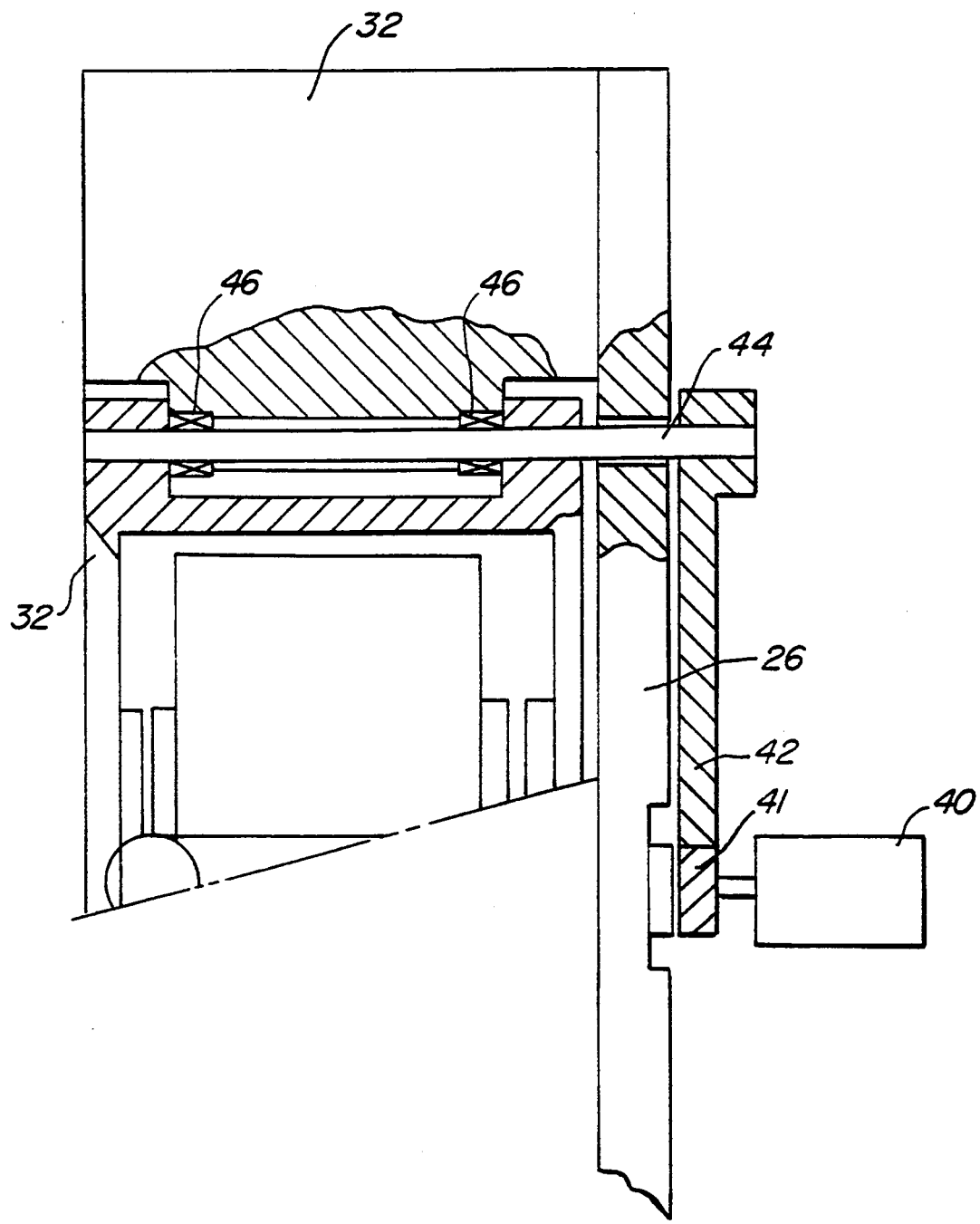
FIG. 4 is a schematic diagram taken along view 3—3' of FIG. 3.

FIG. 3 is taken along view A of FIG. 2A and FIG. 4 is taken along the sideways view 3—3' in FIG. 3. In FIGS. 3 and 4, a pivot motor 40 is mounted on the back of the detector support structure 26 and has a pinion 41 engaged with a detector rotating gear segment 42. The gear segment is attached to the end of a pivot shaft 44 so that the gear segment 42 and pivot shaft 44 rotate together.

The pivot shaft 44 is supported by bearings 46 in the gusset 26*r* and the detector support frame 32 is attached to the pivot shaft 44 so that the detector support frame 32 rotates when the pivot motor is activated to rotate the gear segment 42. A brake 48 is engaged to stabilize the position of the detector and disengaged when the detector is to be pivoted.

The radial motion mechanisms for the pivoting detectors will now be described with reference to FIGS. 5 and 6. FIG. 5 is a view taken along view C of FIG. 2A and FIG. 6 is a view taken along view 5—5' of FIG. 5.

Figure 5:
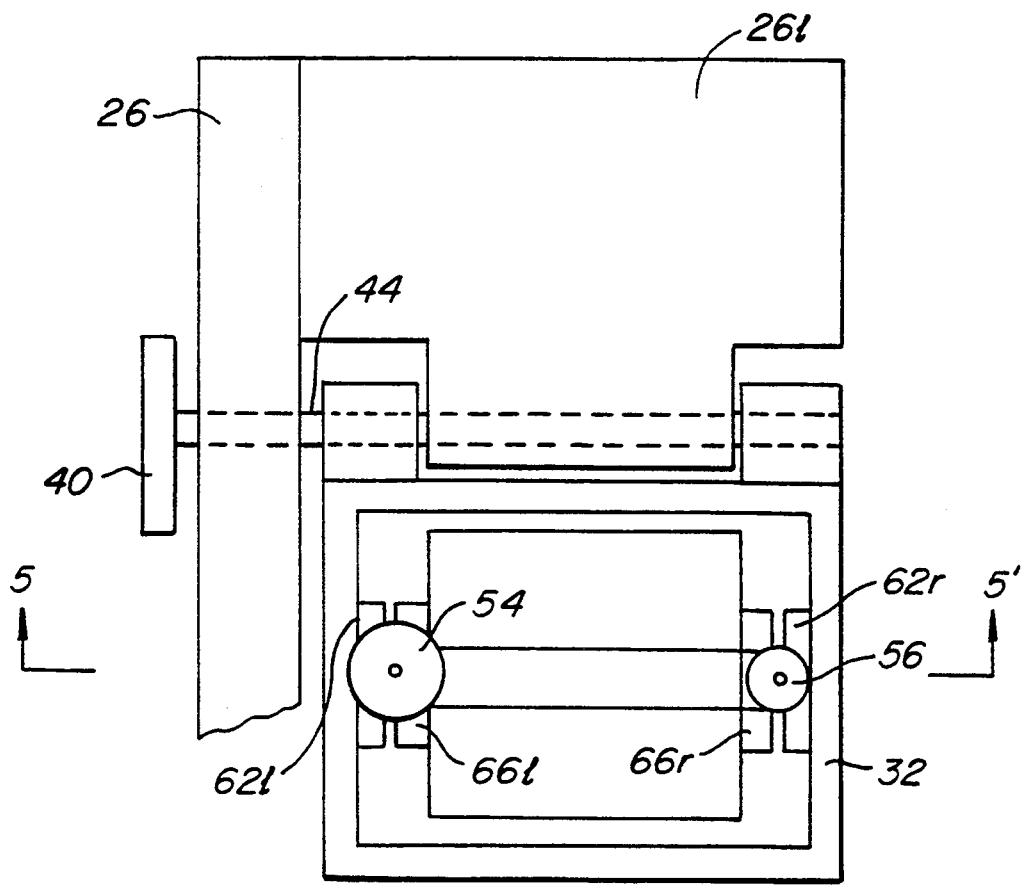
FIG. 5 is a schematic diagram taken along view C of FIG. 2A.
Figure 6:
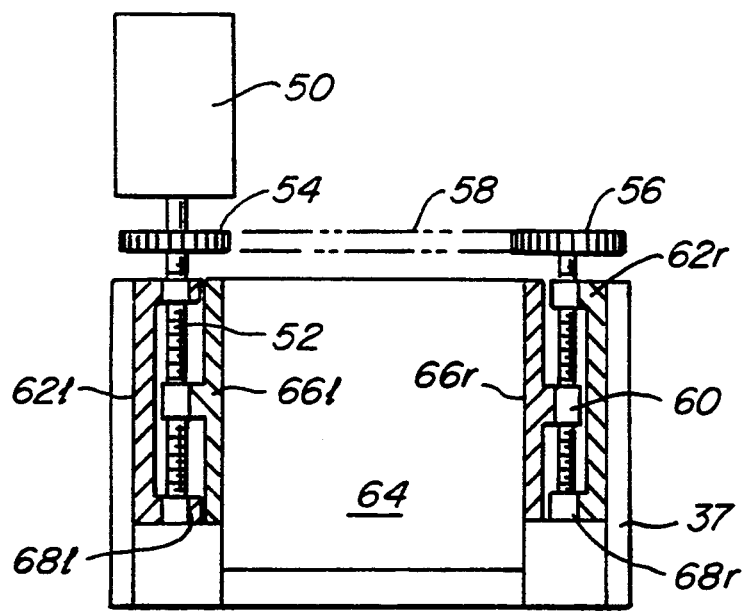
FIG. 6 is a schematic diagram taken along view 5—5' of FIG. 5.

In FIGS. 5 and 6, a radial motion motor 50 rotates a left lead-screw 52, having a transmission sprocket 54 attached thereto, so that the transmission sprocket 54 and left lead-screw 52 rotate together when the radial motion motor 50 is activated. The transmission sprocket 54 is coupled to a drive sprocket 56 by a chain 58. The drive sprocket 56 is coupled to a right lead-screw 60 so that both lead screws rotate together when the motor 50 is activated.

The detector support frame 32 has left and right fixed slide bases 62*l* and 62*r* attached thereto and the detector 64 has left and right movable slide bases 66 attached thereto. The lead-screws 52 and 60 are rotatably supported by bearings 68 mounted in the fixed slide bases 62*l* and 62*r* and are threadably coupled to nuts 70 mounted in the movable slide bases 66*l* and 66*r*.

In operation, the lead-screws 52 and 60 are rotated when the motor 50 is activated to displace the movable slide bases 66*l* and 66*r* due to the rotation of the lead-screws 52 and 60 in the threaded nuts. The direction of displacement is controlled by the direction of motor rotation.

Figure 7:
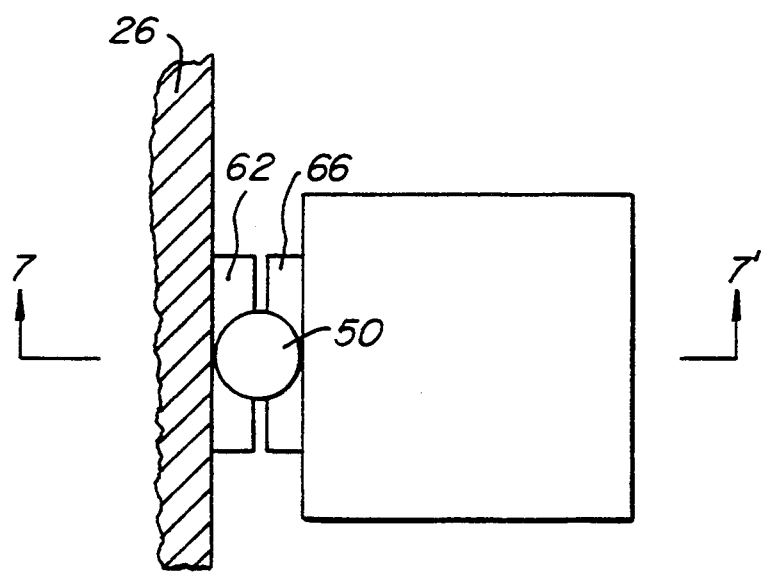
FIG. 7 is a schematic diagram taken along view E of FIG. 2A.

The radial motion mechanisms for the center detector will now be described with reference to FIGS. 7 and 8. FIG. 7 is a view taken along view E of FIG. 2A and FIG. 8 is a view taken along view 7—7' of FIG. 7.

Figure 8:
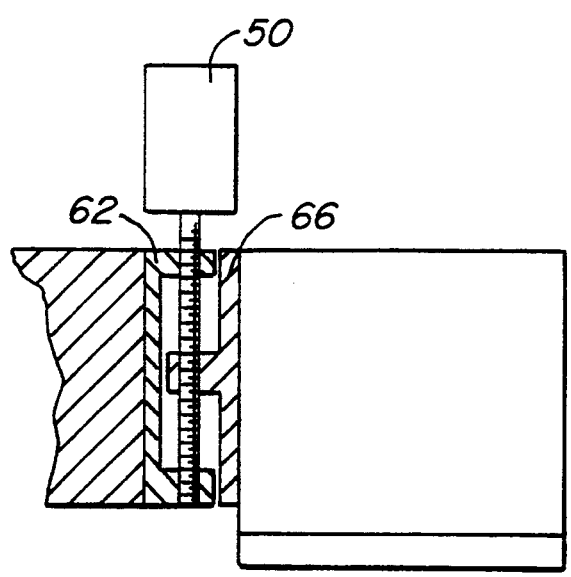
FIG. 8 is a schematic diagram taken along view 7—7' of FIG. 7.

The operation of the radial motion mechanism depicted in FIGS. 7 and 8 is apparent from the description of the operation of the mechanism depicted in FIGS. 5 and 6.

Figure 9:
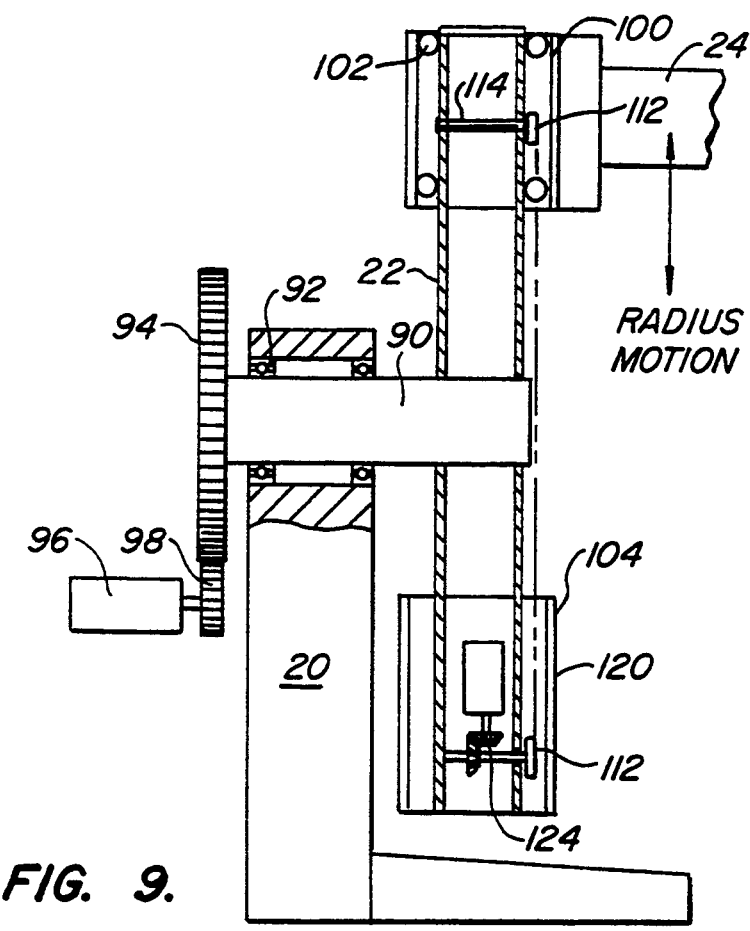
FIG. 9 is a schematic diagram of the base and arm taken along view H of FIG. 2A.
Figure 10:
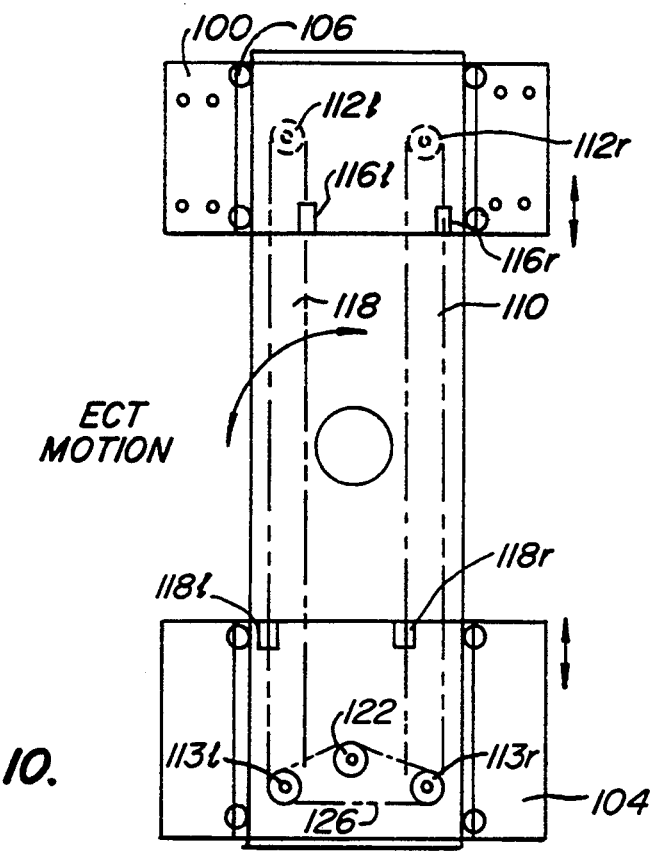
FIG. 10 is a cut away view of the arm mechanism depicted in FIG. 9.

The mechanism for angular and radial displacement of the entire detector assembly will now be described with reference to FIGS. 9 and 10. FIG. 9 is a side, cut-away view of the base 20 and rotatable arm 22 and FIG. 10 is a front, cut-away view of the rotatable arm 22.

In FIG. 9 a shaft 90 is rotatably supported by bearings 92 in the base 20. The shaft 90 has a transmission gear 94 attached to one end and supports the rotatable arm 22 at the other end. An ECT motor 96 is coupled to the transmission gear 94 by a drive gear 98.

In operation, the rotatable arm 22 is rotated when the ECT motor 96 is activated to rotate the detector assembly about the lateral axis thereby adjusting the angular displacement of the detector assembly about the lateral axis.

A support beam guide structure 100 moves along one end of the rotatable arm 22 on guide rollers 102 and a counterweight 104 moves along the other end of the rotatable arm 22 along guide rollers 106.

Support chains 108 and 110 are engaged with support beam and counterweight support sprockets 112 and 113. These support sprockets 112 are fixed on the ends of support shafts 114 supported by bearings in the rotatable arm 22. The support beam guide structure 100 is connected to the right sides of the support chains 108 and 110 by clamps 116 and the counterweight 104 is connected to the left sides of the support chains 108 and 110 by clamps 118.

A radial drive motor 120 is connected to a transmission sprocket 122 by a bevel gear 124. The transmission sprocket 122 is coupled to the counterweight support sprockets 113 by a transmission chain 126.

In operation, when the radial drive motor 120 is activated the counterweight support sprockets are rotated in the same direction to cause the support chains 108 and 110 to move. The support beam guide structure 100 and counterweight 104 move in opposite directions because they are coupled to opposite sides of the support chains 108 and 110.

The opposing motion of the support beam guide structure 100 and the counterweight 104 balances the torques on the rotatable arm 22 to relieve stress and to stabilize the entire system.

The radial motion mechanism depicted in FIG. 9 facilitates the displacement of the detector assembly in a plane perpendicular to the lateral axis 33 without tilting the support beam 24 toward or away from the lateral axis 33. This perpendicular displacement simplifies the SPECT analysis of the image data acquired by the system.

Figure 11:
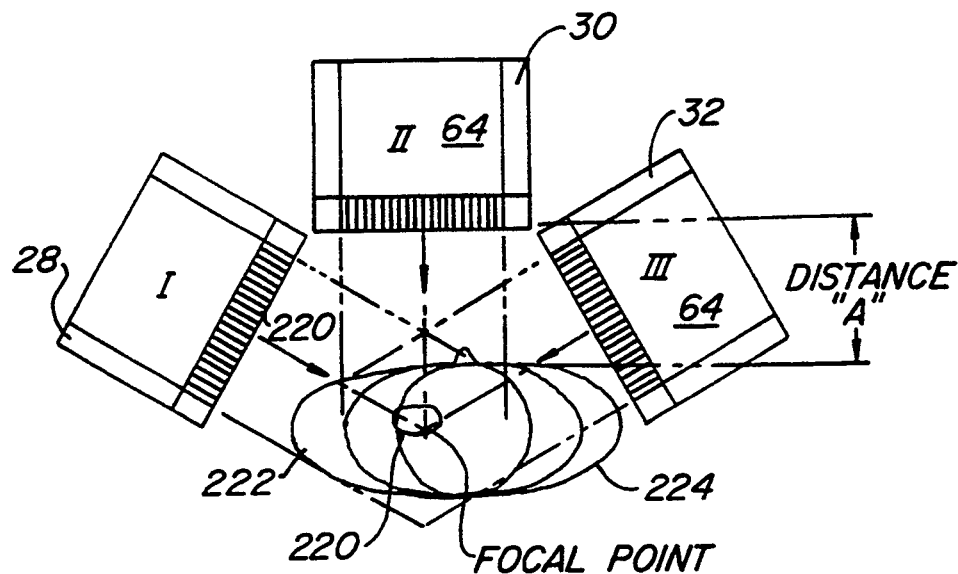
FIG. 11 is a schematic diagram depicting three detectors, having straight collimators, oriented at 60°.
Figure 12:
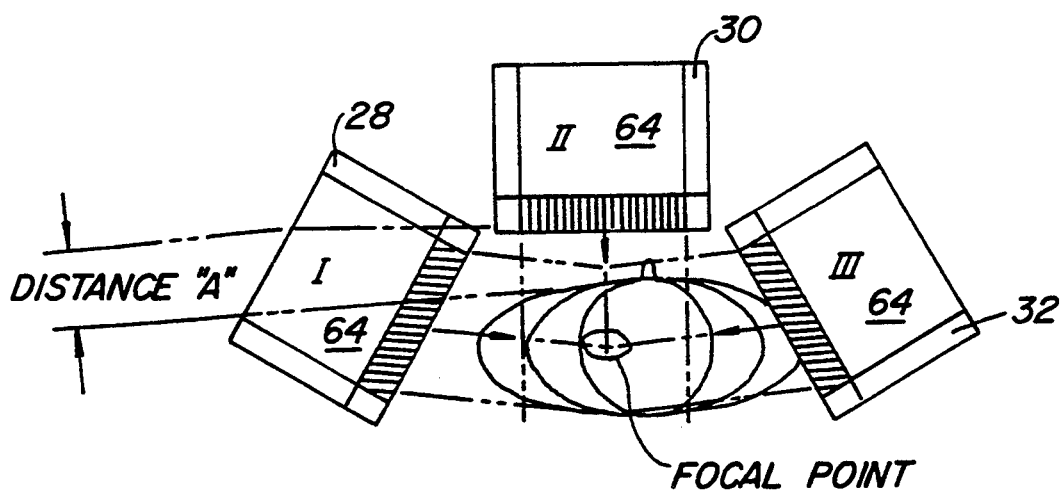
FIG. 12 is a schematic diagram depicting three detectors, having slanted collimators, oriented at 60°.

The use of slanted collimators to reduce the distance between the body of a patient and the collimator of detector II is illustrated by FIGS. 11 and 12.

In FIG. 11 the three detectors are oriented to acquire image data of the heart 220. Each detector 64 has a collimator 222 which guides gamma rays to photo-multiplier tubes inside the detector 64. The slots in collimators 222 are normal to the face 223 of the collimator 222 and the image direction arrows 2, which point to an object-to-be-imaged, are perpendicular to the face 223 of the collimators 222.

In FIG. 11 the detectors I and II have a relative angular displacement of 60°. The distance "A" between detector II and the body 224 of the patient is limited by the physical interference between the detectors and the body of the patient.

In FIG. 12 detectors I and III have slanted collimators where the slots in the collimators 222 are not perpendicular to the face 223 of the collimators 222 but are slanted from the perpendicular by an angle $\gamma$. The image direction arrows 2 for those detectors are parallel to the slots in the slanted collimators 222 and the slots are oriented to reduce the angular displacement between the image direction arrows 2 of the detectors after the detectors have been repositioned to clear the interference between the detectors and the body.

Because of the slanted image direction arrow, detector III can be rotated counter-clockwise and still acquire image data of the heart 220. This counter-clockwise rotation of detector III allows the distance "A" between detector II and the body 224 of the patient to be reduced thereby increasing image resolution. The slanted image direction arrow 2 of detector I remains pointed toward the heart 220 when detector II is moved closer to the body 224 of the patient.

For a detector having slanted collimators offset from the vertical by an offset angle the correction for back projection for a length (L) in the object must be modified to account for the effect of the offset angle.

Figure 13:
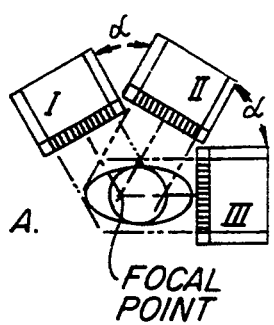
FIGS. 13A–13C, 14A–14C, and 15A–15C are schematic diagrams depicting the orientation of individual detectors at angular stops of 30°, 60°, and 120°.
Figure 13:
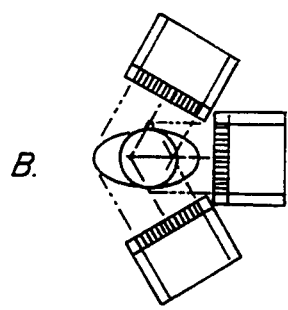
Figure 13:
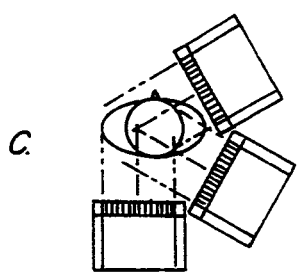
Figure 14:
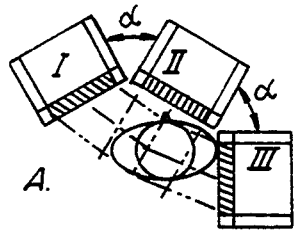
Figure 14:
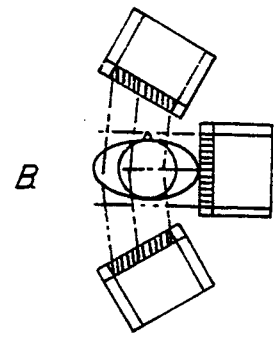
Figure 14:
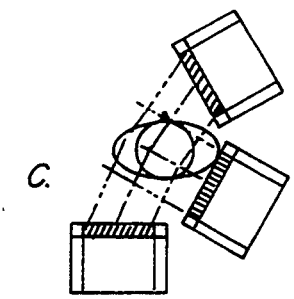
Figure 15:
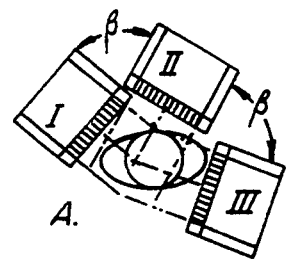
Figure 15:
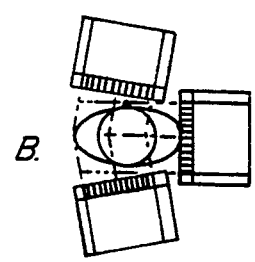
Figure 15:
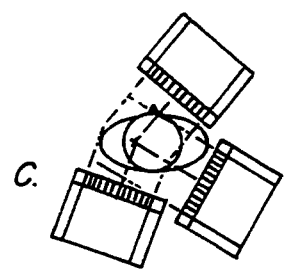

The orientation of the individual detectors for angular stops of 30°, 60°, and 120° in a 180° SPECT scan is illustrated in FIGS. 13–15. The detector assembly is rotated to the correct angle by rotating the rotatable arm 22. The relative angular displacement of the detectors is adjusted by selectively activating the pivot motors 40 and the displacement of the detectors toward or away from the body 224 of the patient is adjusted by selectively activating the radial motion motors 50.

In FIGS. 13 and 14 detectors I and II have a relative angular displacement of magnitude $\alpha$ but slanted collimators are used in FIG. 14. Note that at the 30° stop the detector II is closer to the patient in FIG. 14 than in FIG. 13. This stop is very important because the left anterior oblique (LAO) view, left anterior transverse (LAT) view, and left posterior oblique (LPO) views are simultaneously imaged by detectors I, II, and III respectively. Accordingly, the slanted collimator embodiment is superior at this stop.

In FIG. 15 straight collimators are used but the relative angular distance between detectors I and II is increased to magnitude $\beta$ to decrease the distance between the patient and detector.

In FIGS. 13 and 15 the radial motion mechanisms are utilized to reduce the distance between the detectors and the body 124 of the patient.

The invention has now been described with reference to a preferred embodiment. Alternatives and substitutions will now be apparent to persons of skill in the art. In particular, the preferred embodiment has four degrees of freedom, i.e. independent adjustment of the angular and lateral displacement of the individual detectors and of the detector assembly. For some applications, all degrees of freedom may not be required. Additionally, well-known mechanical equivalents for some of the described motion mechanisms may be substituted. Thus, it is not intended to limit the invention except as provided by the appended claims.

What is claimed is:

1. An imaging system for acquiring image data required to generate an image of an object, said system comprising:

a detector support structure having a major face and a right and a left detector support, each protruding along a lateral axis perpendicular to said major face of said support structure;

first, second, and third detectors, each housed in a rectangular detector support frame coupled to said support structure and characterized by a substantially planar collimator surface for receiving incident radiation and with said surface disposed perpendicular to the direction the detector is pointed;

a first angular displacement mechanism, coupled to a first corner mechanical interface of the first and second detector support frames, providing a range of relative angular displacement about an axis passing through said first corner and parallel to the lateral axis of 60° to 120° between said collimator surfaces of said first and second detectors;

a second angular displacement mechanism, coupled to a second corner mechanical interface of the second and third detector support frames, providing a range of relative angular displacement about an axis passing through said second corner and parallel to the lateral axis of 60° to 120° between said collimator surfaces of said second and third detectors;

a first radial displacement mechanism, coupled to said first detector for displacing said first detector toward or away from the object;

a second radial displacement mechanism, coupled to said second detector for displacing said second detector toward or away from the object;

a third radial displacement mechanism, coupled to said third detector for displacing said third detector toward or away from the object, where said first, second, and third detectors, said detector support frames, said first and second angular displacement mechanisms and said first, second, and third radial displacement mechanisms comprise a detector assembly;

means, coupled to said detector assembly, for displacing said detector assembly toward or away from the lateral axis; and means, coupled to said means for displacing, for rotating said detector assembly about the lateral axis.

2. The system of claim 1 wherein said means for rotating and said means for displacing said detector assembly comprises:

a base;

a shaft rotatably mounted in said base and oriented along the lateral axis;

a rotation arm mounted to a first end of said shaft which rotates with said shaft;

a shaft rotation mechanism, mounted to a second end of said shaft, for rotating said shaft and said rotation arm through a selected angle about the lateral axis;

a support arm having a first end movably coupled to a first end of said rotation arm and having a second end coupled to said detector support structure;

a counterweight movably coupled to a second end of said rotation arm; and radial actuation means for selectively displacing said support arm and counterweight to displace said detector assembly toward or away from the lateral axis in equal increments to maintain the balance of said rotation arm.

3. An imaging system for acquiring image data required to generate an image of an object, said system comprising:

a detector support structure having a major face and a right and left detector support, each protruding along a lateral axis perpendicular to said major face of said support structure;

means for rotating said detector support structure about the lateral axis;

means, coupled to said means for rotating, for displacing said detector support structure toward or away from the lateral axis;

first, second, and third detectors, each housed in a rectangular detector support frame coupled to said support structure and characterized by a substantially planar collimator surface for receiving incident radiation and with said surface disposed perpendicular to the direction the detector is pointed;

a first angular displacement mechanism, coupling a lower edge of the first detector support frame to said detector support structure, for adjusting the angular displacement about an axis passing through said lower edge and parallel to the lateral axis from a range of 60° to 120°, relative to the lateral axis, between the collimator surfaces of said first and second detectors;

a second angular displacement mechanism, coupling a lower edge of the third detector support frame to said detector support structure, for adjusting the angular displacement about an axis passing through said lower edge and parallel to the lateral axis from a range of 60° to 120°, relative to the lateral axis, between the collimator surfaces of said second and third detectors;

a first radial displacement mechanism, coupled to said first detector and said first angular displacement mechanism, for displacing said first detector toward or away from the object;

a second radial displacement mechanism, coupling the second detector to the detector support structure, for moving said second detector toward or away from the object; and a third radial displacement mechanism, coupled to said third detector and said third angular displacement mechanism, for displacing said third detector toward or away from the object.

4. An imaging system for acquiring image data required to generate an image of an object, said system comprising:

a detector support structure having a major face and a right and a left detector support, each protruding along a lateral axis perpendicular to said major face of said support structure;

first, second, and third detectors, each detector including a collimator having a substantially planar surface disposed perpendicular to the direction the detector is pointed and slots for guiding radiation emitted by the object with parallel slots of said first and third detectors slanted by a fixed angle from the normal to said planar face and parallel slots of said second detector parallel to the normal to said planar face to reduce the angular displacement between the slots of said first and second detectors;

a first angular displacement mechanism, coupled to a first corner mechanical interface of first and second detector support frames, providing a range of relative angular displacement about an axis passing through said first corner and parallel to the lateral axis of 60° to 120° between said collimator surfaces of said first and second detectors;

a second angular displacement mechanism, coupled to a second corner mechanical interface of said second detector support frame and a third detector support frame, providing a range of relative angular displacement about an axis passing through said second corner and parallel to the lateral axis of 60° to 120° between said collimator surfaces of said second and third detectors;

a first radial displacement mechanism, coupled to said first detector support frame, for displacing said first detector toward or away from the object;

a second radial displacement mechanism, coupled to said second detector support frame, for displacing said second detector toward or away from the object;

a third radial displacement mechanism, coupled to said third detector support frame, for displacing said third detector toward or away from the object, where said first, second, and third detectors, said detector support frames, said first and second angular displacement mechanisms and said first, second, and third radial displacement mechanisms comprise a detector assembly;

means, coupled to said detector assembly, for displacing said detector assembly toward or away from the lateral axis; and means, coupled to said means for displacing, for rotating said detector assembly about the lateral axis where the slanted collimator slots of said first detector facilitate reducing the distance between the collimator of the second detector and the object when the object is non-circular and the second detector is oriented to take an anterior view of the object.

5. An imaging system for acquiring imaging data generated by an object positioned about a lateral axis, said system comprising:

a support structure having a substantially planar major face and a right and a left detector support, each protruding along the lateral axis perpendicular to said major face of said support structure;

means for supporting said support structure and for orienting said major face of said support structure along a first plane substantially perpendicular to the lateral axis;

means, coupled to said means for supporting, for angularly displacing said support structure about the lateral axis;

means, coupled to said means for supporting, for displacing said support structure toward or away from the lateral axis;

means for mounting a first detector, characterized by a substantially planar collimator surface for receiving incident radiation and with said surface disposed perpendicular to the direction said first detector is pointing, on said left detector support of said support structure so that the first detector collimator surface is oriented perpendicular to said first plane;

means for mounting a second detector, characterized by a substantially planar collimator surface for receiving incident radiation and with said second detector collimator surface disposed perpendicular to the direction said second detector is pointing, on said major face of said support structure so that the second detector collimator surface is oriented perpendicular to said first plane;

means for mounting a third detector, characterized by a substantially planar collimator surface for receiving incident radiation and with said third detector collimator surface disposed perpendicular to the direction said third detector is pointing, on said right detector support of said support structure so that the third detector collimator surface is oriented perpendicular to said first plane and where said second detector is mounted between said first and third detectors.

6. The system of claim 5 wherein:
said means for mounting said first detector further comprises means for pivoting the first detector to change the orientation of the first detector collimator surface.

7. The system of claim 5 wherein:
said means for mounting said first detector further includes means for moving said first detector along a path perpendicular to its collimator surface.

8. An imaging system for acquiring imaging data generated by an object positioned about a lateral axis, said system comprising:

a base;

a shaft, having first and second ends, with the first end rotatably mounted in said base and having an axis of rotation substantially coincident with the lateral axis;

a first detector characterized by a substantially planar collimator surface for receiving incident radiation and with said surface disposed perpendicular to the direction said first detector is pointing;

a second detector characterized by a substantially planar collimator surface for receiving incident radiation and with said second detector collimator surface disposed perpendicular to the direction said second detector is pointing;

a third detector characterized by a substantially planar collimator surface for receiving incident radiation and with said third detector collimator surface disposed perpendicular to the direction said third detector is pointing;

an arm, mounted on the second end of said shaft and having first and second ends and a major face oriented in a first plane perpendicular to the lateral axis;

a support structure, having a major surface oriented along the first plane, for supporting said first, second, and third detectors;

means, connecting said support structure and said arm, for moving said support structure toward or away from the lateral axis; and means, coupled to said shaft, to rotate said shaft to angularly displace the support structure about the lateral axis.

9. The system of claim 8 further comprising:
means for pivotally mounting said first detector on said support structure.

10. The system of claim 9 further comprising:
means, coupled to said means for pivotally mounting, for displacing said first detector along a path perpendicular to said first detector collimator surface.

11. The system of claim 10 further comprising a collimator mounted on said first detector having parallel slots slanted by a fixed angle from the normal to the direction said first detector collimator face is pointed.

* * * * *